United States Patent [19]
Vedamuthu et al.

[11] Patent Number: 6,063,410
[45] Date of Patent: May 16, 2000

[54] METHOD AND COMPOSITIONS FOR IMPROVED FLAVOR AND AROMA IN FERMENTED MEAT

[75] Inventors: Ebenezer R. Vedamuthu, Rochester, Minn.; Angels Trius, Bussum; Petronella A. P. Vlegels, Huezen, both of Netherlands

[73] Assignee: Quest International Flavors & Food Ingredients Company, division of Indopco, Inc., Bridgewater, N.J.

[21] Appl. No.: 09/042,884

[22] Filed: Mar. 17, 1998

[51] Int. Cl.$^7$ ............... A23L 1/317; A23L 1/318; A23L 1/231; A23L 1/23; C12N 1/20

[52] U.S. Cl. ............... 426/56; 426/59; 426/61; 426/105; 426/534; 435/252.4; 435/252.9; 435/253.4

[58] Field of Search ............... 426/56, 61, 59, 426/574, 641, 105, 534; 435/252.4, 252.9, 253.4

[56] References Cited

U.S. PATENT DOCUMENTS

| | | | |
|---|---|---|---|
| 1,380,068 | 5/1921 | Kurk | 426/56 |
| 3,193,391 | 7/1965 | Jansen et al. | 99/157 |
| 3,561,947 | 2/1971 | Olsen et al. | 99/109 |
| 3,814,817 | 6/1974 | Everson et al. | 426/56 |
| 3,960,664 | 6/1976 | Olsen et al. | 195/59 |
| 4,013,797 | 3/1977 | Gryczka | 426/56 |
| 4,147,807 | 4/1979 | Gryczka et al. | 426/56 |
| 4,303,679 | 12/1981 | Raccach | 426/59 |

FOREIGN PATENT DOCUMENTS

| | | |
|---|---|---|
| 1692174 | 8/1966 | Germany. |

OTHER PUBLICATIONS

Varnam, A.H., and J.P. Sutherland, Meat and Meat Products: technology, chemistry and microbiology, Ch. 7:317–353 (1995).

Hinrichsen, L., and H.J. Anderson, Volatile Compounds and Chemical Changes in Cured Pork: Role of Three Halotolerant Bacteria, J. Agri Food Chem 42:1537–1542 (1994).

Hinrichsen, L. and S.B. Pedersen, Relationship among Flavor, Volatile Compounds, Chemical changes, and Microflora in Italian–Type Dry–cured Ham During Processing, J. Agric. Food Chem 43:2932–2940 (1995).

Hierro, E., et al, Effect of Selected Micro–organisms on Dry Fermented Sausage Volatiles, Proceedings 41st Annual International Congress of Meat Science and Technology 1:251–252 (1995).

Berdagué, et al, Effects of Starter Cultures on the Formation of Flavour Compounds in Dry Sausage, Meat Science 35:275–287 (1993).

Kemner, M.K. et al, Aroma Formation with Starter Cultures in Meat Model Systems, Med. Fac. Landbouww. Univ. Gent 60/4a (1995).

Stanhke, L.H., Dried Sausages Fermented with *Staphylococcus xylosus* at Different Temperatures and with Different Ingredient Levels—Part III. Sensory Evaluation, Meat Science 41:211–223 (1995).

Andersen, H., and L., Hinrichsen, Changes in Curing Agents, Microbial Counts and volatile Compounds during Processing of Green Bacon using Two Different Production Technologies, J. Sci Food. Agric. 68:477–487 (1995).

Hagen, B.F., et al Addition of a bacterial Proteinase Reduces the Maturation Time of Dry Fermented Sausages., Abstract, 5th Symposium on lactic acid bacteria, Genetics, Metabolism and Application, Veldhoven, Holland, Sep. 1996.

MacLeod P. and M.E. Morgan, Leucine Metabolism of *Streptococcus lactis* var. Maltigenes. I. Conversion of Alpha–Ketoisocaproic Acid to Leucine and 3–Methyl butanal, pp. 1208–1214 (1955).

Miller, A., et al *Lactobacillus maltaromicus*, A new species Producing a Malty Aroma, Intern. J. of System. Bacterio. 24:346–354 (1974).

*Primary Examiner*—Keith D. Hendricks
*Attorney, Agent, or Firm*—Ian C. McLeod

[57] ABSTRACT

Malty flavor producing cultures are used in meat fermentations to produce flavor, particularly 3-methyl-butanal, are described. Mixed cultures used for producing the fermented meats, including Pediococcus, Micrococcus and the malty flavor producing culture, a Lactococcus or Lactobacillus, are described.

47 Claims, 3 Drawing Sheets

METHOD AND COMPOSITIONS FOR IMPROVED FLAVOR AND AROMA IN FERMENTED MEAT

BACKGROUND OF THE INVENTION (1) Field of the Invention

The present invention relates to the use of a food grade bacteria which produces 3-methyl-butanal for the preparation of a fermented meat product. This invention particularly relates to the process for developing an improved flavor and aroma in fermented meat particularly in dry or semi-dry sausages using a bacterial composition of a culture which produces 3-methyl-butanal. The present invention relates in one specific embodiment, to a method and compositions for producing fermented meats using a lactic acid producing culture in combination with a culture which produces 3-methyl-butanal and optionally with a culture(s) which produces red color. Alternatively, the culture which produces 3-methyl-butanal can be used to develop flavor in the meat and relying on the culture to produce lactic acid.

(2) Description of Related Art

Processes for dry and semi-dry sausage preparation are examples of conventional fermentations where acidity is generated to provide tang. Dry and semi-dry sausages vary in taste according to the meat source, i.e., pork, beef, veal, etc. and their different mixtures, the sugar, spices, and starter cultures used in processing. The fairly distinct categories of semi-dry sausage are known as summer sausage, cervelat, Thuringer, pork roll and lebanon bologna. Some dry sausages are Chorizos, hard salami, Genoa salami, German katenwurst, and Mettwurst salamis and various kind of Italian sausage such as Pepperoni and Cappicola. There are other dry and semi-dry sausages which can be produced by the present invention.

Dry and semi-dry sausages are generally distinguished from other types of sausages by the prior art in that they are fermented. The comminuted meat mixture is preferably mixed with added salt, spices, edible nitrite and/or nitrate for curing bacteria and sometimes acid forming chemicals. It is then stuffed into casing and fermented with the bacteria. Curing allows the edible nitrites, and nitrates upon subsequent reduction to nitrite, to form nitric oxide which in the presence of acids combines with the pigment in the meat to produce the red color usually associated with the sausage. It is the edible nitrites which generate the red color in the meat and more importantly which provide protection against the formation of botulism toxin by *Clostridium botulinum* growth (Varnam, A. H., and J. P. Sutherland Meat and meat products: technology, chemistry and microbiology, Chapter 7:317–353 (1995)). The meat can also be uncured.

The fermented sausage may be given a light or heavy smoke. The semi-dry sausages are sometimes cooked after the fermentation without an extensive drying period. The dry sausage is dried for various time periods under controlled humidity and temperature conditions, depending upon the nature of the end product. Because of this processing, the resulting sausages differ from other types of sausage, such as fresh, smoked, cured, cooked and the so-called new condition sausages.

A commonly used starter bacterium for fermenting meat to produce semi-dry or dry sausage is *Pediococcus acidilactici* because it rapidly produces large amounts of primarily lactic acid to lower the pH, which gives the final sausage its characteristic tang. This bacterium is commercially obtainable both in a frozen state as a concentrate and in a lyophilized state. It may be for instance the bacterium described in U.S. Pat. Nos. 3,561,977 and 3,960,664 to Olsen et al. U.S. Pat. No. 4,303,679 to Raccach describes the use of *Pediococcus pentosaceus* and metal salts for fermenting meats. U.S. Pat. No. 3,814,817 to Everson et al describes the use of *Lactobacillus plantarum* for fermenting meat.

Species of Micrococcus are also used in making sausage, particularly in Germany. W. German Patent No. 1,692,174 describes an unidentified strain of Micrococcus mixed with lactic acid forming bacteria, with substantial amounts of gluconic acid delta lactone (GDL) to rapidly lower the pH, and with polyphosphates, ascorbic acid and its sodium salts as pH regulators. GDL has a chemical acid taste and is undesirable for this reason.

The Micrococcus produce the red sausage color during the fermentation as discussed above. Microbiology Vol 26, No. 4 pp. 489 to 496 (1973) and U.S. Pat. No. 1,380,068 describe the importance of the naturally occurring micrococci in the meat on color development. U.S. Pat. No. 4,013,797 to Gryczka also describes the importance of using a high acid producing nitrate reducing bacteria characterized as Micrococcus sp. NRRL-B-8048. U.S. Pat. No. 4,147,807 to Gryczka et al describes the use of *Micrococcus varians* to develop the red color in meat.

U.S. Pat. No. 3,193,391 describes the use of various flavor producing bacteria from the families Lactobacillaceae and Micrococcaceae for preparing cured meats. This is a related fermentation process for flavor development on large sized meat sections.

Starter cultures play several important roles in the fermentation and ripening of dry and semi-dry sausages. The primary function of the starter culture is the acidification process by means of converting the sugar(s) added to the meat mixture into acid. Usually, the sugars added are glucose or sucrose. The acid produced through this fermentation (primarily lactic acid) contributes to the tanginess (acid taste) of the product, promotes water release as the pH is depressed to the iso-electric point of meat proteins to attain the desired final water activity ($a_w$), provides safety against food-borne pathogens or production of enterotoxins, contributes to the final texture by the modification of meat proteins, and also plays a part in the fixing of the red color of meat. The acid producing starter cultures usually used belong to the genera Pediococcus and Lactobacillus. Only species that are relatively salt tolerant are used.

The secondary functions of starter bacteria used in dry and semi-dry sausages relate to the nitrate reducing activity which plays an important role in maintaining the red color, dissipating hydrogen peroxide generated by certain indigenous and contaminant lactic acid bacteria, and generating flavor compounds which impart the "mature sausage flavor". Hydrogen peroxide has deleterious effects on color and on fat by reacting with the red meat pigment and turning it to a green hue. As a powerful oxidant, it is also responsible for reacting with the fat to generate oxidized flavors. Therefore, the use of nitrate reducing and catalase producing genera in starter mixtures ensures good red color fixation and prevention of oxidized flavor defects. The bacterial species commonly used for these functions are *Micrococcus varians* (some authors include *Micrococcus roseus*) and *Staphylococcus carnosus* and *Staphylococcus xylosus*.

The flavor of sausages is derived from the salt, spices, acid generated by fermentation, various secondary metabolites of carbohydrate fermentation and by-products of proteolytic and lipolytic activity of starter and adventitious flora. Lactic acid bacteria used as starters have relatively mild proteolytic and lipolytic/esterolytic activities, while the micrococci and staphylococci possess more pronounced proteolytic and lipolytic enzymes. Peptides and amino acids derived through lactic acid bacterial metabolism could further be transformed into flavorful carbonyls, alcohols and esters by the micrococci and staphylococci. Proteolytic and lipolytic activities of the micrococci and/or staphylococci add on to these flavor imparting pool of components.

The flavor chemistry of fermented sausages and hams is quite complex. Berdague et al found more than 86 compounds that comprised the flavor components of dry sausages that were made without spices or other flavoring materials. These workers suggested that the origin of volatile flavor compounds in fermented sausages were the result of lipid oxidation (60%), fermentation (27%), proteolysis (6%) and other sources (7%). Stahnke and Zeuthen examined the volatiles from Italian Salami. They mentioned that some of the flavorful volatiles originate from spices, and others are degradation products of carbohydrates, protein and lipids brought about by microbial activity. They also stated that proteolytic breakdown products like free amino acids, peptides and nucleotides have a pronounced effect on the final taste of salamis, while lipolytic breakdown products like volatile fatty acids, aldehydes and ketones are of more importance to the aroma. The contribution of secondary metabolism of amino acids to the carbonyl and volatile fatty acid pool should also be considered to be significant in the flavor of fermented meats.

Among the more prominent flavor compounds in fermented sausages and hams mentioned by various investigators are two aldehydes: 3-methyl-butanal and 2-methyl butanal, (Hinrichsen L. and H. J. Anderson, Volatile Compounds and Chemical Changes in Cured Pork: Role of Three Halotolerant Bacteria, J. Agri. Food Chem. 42:1537–1542 (1994)); (Hinrichsen L. and S. B. Pedersen, Relationship among Flavor, Volatile Compounds, Chemical Changes, and Microflora in Italian-Type Dry-cured Ham During Processing, J. Agric. Food Chem 43:2932–2940 (1995)); (Hierro, E. et al, Effect of Selected Microorganisms on Dry Fermented Sausage Volatiles, Proceedings 41st Annual International Congress of Meat Science and Technology 1:251–252 (1995)); (Berdagué et al, Effects of Starter Cultures on the Formation of Flavour Compounds in Dry Sausage, Meat Science 35:275–287 (1993)); (Kemner, M. K. et al, Aroma Formation with Starter Cultures in Meat Model Systems, Med. Fac. Landbouww. Univ. Gent 60/4a (1995)); (Stanhke, L. H., Dried Sausages Fermented with *Staphylococcus xylosus* at Different Temperatures and with Different Ingredient Levels—Part III. Sensory Evaluation, Meat Science 41:211–223 (1995); and (Andersen, H., and L. Hinrichsen, Changes in Curing Agents, Microbial Counts and Volatile Compounds during Processing of Green Bacon using Two Different Production Technologies, J. Sci. Food. Agric. 68:477–487 (1995)). Hinrichsen and Andersen have discussed the various metabolic routes by which these methyl side-chain aldehydes could be derived. One of these pathways involves the deamination of the amino acid leucine followed by oxidative decarboxylation of the intermediate alpha-ketoisocaproate.

While Berdague et al describe the odor of 3-methyl-butanal as "rancid, sweaty, pungent", Hinrichsen and Pedersen report that this aldehyde may contribute to the "nutty, cheesy" notes of sausage flavor. Recently, Hagen et al, (Hagen, B. F., et al Addition of a bacterial Proteinase Reduces the Maturation Time of Dry Fermented Sausages., Abstract, 5th Symposium on lactic acid bacteria, Genetics, Metabolism and Application, Veldhoven, Holland, September 1996), reported on the use of a bacterial proteinase derived from *Lactobacillus paracasei* ssp. *paracasei* NCDO 151 to accelerate dry sausage ripening. They obtained higher sensory scores on maturity of flavor, color, hardness and other attributes. They noted that the concentration of 3-methyl-butanal and 2-methyl butanal were higher in the enzyme-containing sausages. It is preferred to use cultures rather than enzymes which must appear on the label.

The availability of free leucine in sausage systems inoculated with pediococci and micrococci was reported by Varnam and Sutherland (Varnam, A. H., and J. P. Sutherland, Fermented Sausages, Meat and meat products: technology, chemistry and microbiology Chapter 7:317–353 (1995)). This is important as background for the production of 3-methyl-butanal in fermented meat. In the dairy culture art, the production of 3-methyl-butanal by "malty" strains of *Lactococcus lactis* spp *lactis* was elucidated by MacLeod and Morgan (MacLeod P. and M. E. Morgan, Leucine Metabolism of *Streptococcus lactis* var. Maltigenes. I. Conversion of Alpha-Ketoisocaproic Acid to Leucine and 3-methyl-butanal, pages 1208–1214 (1955)). For a long time, such strains were named *Streptococcus lactis* var. *maltigenes*. Such strains could commonly be isolated from raw milk. These bacteria convert leucine to 3-methyl-butanal by deamination, followed by oxidative decarboxylation. In 1974, Miller et al, (Miller A., et al *Lactobacillus maltaromicus,* a New species Producing a Malty Aroma, Intern. J. Of System. Bacterio. 24:346–354 (1974)) described a raw milk lactobacilli that also produced a "malty" flavor in milk and broth systems. The "malty" flavor in this case was also attributed to 3-methyl-butanal. The organism was named *Lactobacillus maltaromicus.* A metabolic pathway similar to the lactococci may be operative in this Lactobacillus spp.

The use of lactococci or lactobacilli in general as acid producing starters in sausage systems is not favored because of their relative low salt tolerance. Lactococci or lactobacilli do not thrive at salt concentrations greater than 6.0%. In sausage systems, the brine salt concentration is around 6.0 to 6.5%. The application of malty lactococci or lactobacilli as an adjunct starter solely for flavor generation without acid production has not been so far considered in making fermented sausages.

OBJECTS

It is therefore an object of the present invention to provide a process for producing a fermented meat with an excellent flavor and color where a malty dairy culture is used for generating flavor, contrary to the teachings of the prior art. It is also an object of this invention to provide unique bacterial compositions for use in the process. It is particularly an object of the present invention to provide bacterial concentrates which produce fermented meat wherein the pH and flavor of the fermentate can be varied by using mixtures of bacteria in various ratios. These and other objects will become increasingly apparent by reference to the following description.

DESCRIPTION OF PREFERRED EMBODIMENTS

The present invention relates to a meat fermentation, the improvement which comprises: mixing a culture selected from the group consisting of a Lactococcus and a Lactobacillus which produces 3-methyl-butanal with the lactic acid producing bacterium in the meat in cell numbers which provides flavor and aroma in the fermented meat; and fermenting the meat to produce the fermented meat. While it is clear that 3-methyl-butanal is a principal flavor producing product of the culture, obviously other flavor and aroma compounds are also produced. The selection of one culture over another depends upon the results desired. Also other sources of flavor and aroma (volatiles) can be added to the meat before or after fermentation. Various other flavor producing strains can also be included.

The present invention in one preferred form relates to a meat fermentation method including the steps of providing a lactic acid producing bacterium with an assimilable sugar in the meat so that the lactic acid is produced from the sugar over a period of time to produce the fermented meat, the improvement which comprises: mixing a culture selected from the group consisting of a Lactococcus and a Lactobacillus which produces 3-methyl-butanal with the lactic acid producing bacterium in the meat in cell numbers which provides flavor and aroma in the fermented meat; and fermenting the meat to produce the fermented meat. Another form is to use the culture which produces the 3-methyl-butanal as the sole source of lactic acid.

The present invention relates to a preferred bacterial culture for meat fermentation which comprises: a lactic acid producing bacterium which produces the lactic acid from an assimilable sugar in the meat; and a culture selected from the group consisting of a Lactococcus and a Lactobacillus which produces 3-methyl-butanal in the meat in cell numbers which provides flavor and aroma when mixed in the fermented meat. The culture preferably contains between $10^6$ and $10^{12}$ CFU per ml.

The "malty flavor" of the present invention in the fermented meat, is associated with the production of the 3-methyl-butanal. Numerous other compounds are produced as well; however, 3-methyl-butanal functions to "finger print" the particular Lactococcus or Lactobacillus culture to be used.

The preferred Lactococcus lactis spp lactisNRRL-B-21904 was deposited with the Northern Regional Research Laboratory, Peoria Ill. 61604 on Dec. 11, 1997. Lactobacillus maltaromicus ATCC 27865 is available from the American Type Culture Collection. They are available upon request by name and deposit number. All restrictions on the distribution of the deposited strain will be irrevocably removed on granting of a patent on this application.

The method particularly includes a meat fermentation method including the steps of providing lactic acid producing bacteria in the meat with an assimilable carbohydrate and with nitrate and/or nitrite and then fermenting the meat with the bacteria so that lactic acid is produced from the carbohydrate over a period of time in the fermented meat. Preferably this is accomplished by providing in admixture in the meat a culture of a selected *Pediococcus pentosaceus* at a concentration of between about $10^5$ and $10^9$ of the *Pediococcus pentosaceus* and a culture selected from the group consisting of a malty flavor producing Lactococcus, a Lactobacillus and mixtures thereof, which produce 3-methyl-butanal in the fermentation. Preferably the meat mixture is fermented at meat temperatures between about 15.6° C. (60° F.) and 26.7° C. (80° F.) to produce a pH less than about 5; and fermenting the meat admixture at smokehouse temperatures between about 15.6° C. (60° F.) and 48.9° C. (120° F.) with the *Pediococcus pentosaceus* so that lactic acid and 3-methyl-butanal are produced in the fermented meat product.

The composition particularly includes a culture which comprises a selected *Pediococcus pentosaceus* grown in a first growth medium including assimilable sources of carbon, nitrogen and inorganic substances, including preferably a manganese salt, to a concentration of at least about $1 \times 10^7$ of the *Pediococcus pentosaceus* per ml, having a pH between about 4 and 7. The culture contains a stimulatory, food grade metal salt after growth in an amount sufficient to accelerate the fermentation in the meat by providing a concentration of metal ion between about 0.01 ppm and 1500 ppm in the meat. The preferred *Pediococcus pentosaceus* culture is characterized by an ability to rapidly ferment in a meat admixture with an assimilable sugar and nitrates and/or nitrites in a range between 15.6° C. (60° F.) and 26.7° C. (80° F.) to produce a pH less than about 5. The *Pediococcus pentosaceus* is mixed with the malty flavor producing culture selected from the group consisting of a Lactococcus, a Lactobacillus and mixtures thereof grown in a general growth medium including assimilable sources of carbon, nitrogen and inorganic substances, which produce 3-methyl-butanal in the meat fermentations. The ratio of the Pediococcus to malty flavor producing culture by cell count is preferably between 1.0 to 0.01 and 0.01 to 1.0.

The metal salt is used with the *Pediococcus pentosaceus* in amounts of metal cation in the salt above about 0.01 ppm to about 1500 ppm by weight of the meat, preferably between about 0.1 and 100 ppm. The salt must be stimulatory and food grade. Such salts include for instance manganese chloride, manganese sulfate, manganese citrate, manganese glycerophosphate, manganese oxide and manganese gluconate and the various non-toxic metal salts of acids which are at least slightly soluble in water. Other metal ions include ferrous, ferric, magnesium, calcium, zinc; however, none are as effective as manganese. The metal salt can be incorporated into the culture in an amount between about 0.01 percent and 50 percent by weight of the culture in order to provide the amount of the metal salt needed in the meat when the culture is added.

The preferred *Pediococcus pentosaceus* strain of the present invention has been deposited at the Northern Regional Research Laboratory of the USDA, Peoria Ill., and has been designated as NRRL-B-11,465. NRRL-B-11,465 or a strain of the same species which has substantially the same low meat temperature fermentation characteristics is used in the present invention, such as those produced by genetic manipulation including mutation. There are no restrictions on the distribution of the culture by the NRRL.

The selected *Pediococcus pentosaceus* cells can be used as a concentrate containing at least about $1 \times 10^7$ cells per ml, usually between about $1 \times 10^9$ and $5 \times 10^{11}$ cells per ml mixed with the metal salt, preferably manganese salts. Concentrates with less than about $1 \times 10^7$ cells per ml require too much volume of culture because of excess water addition to the resultant sausage. The concentrate containing the metal salt can be frozen with or without a freezing stabilizing agent such as monosodium glutamate, malt extract, low fat dry milk, alkali metal glycerophosphates, glutamic acid, cystine, glycerol or dextran or the like and then thawed for use or it can be lyophilized to a powder as is well known to those skilled in the art. The cells are used at a rate between about $10^5$ and $10^9$ cells per gram of meat.

As used herein the term "red color" means the color associated with presently marketed fermented sausages and processed meats as accepted in the trade. It is easily distinguished from the gray color of untreated aged meat. Also edible nitrites initially produce a gray color when mixed with meat which changes to a red color over a period of time as is well known to those skilled in the art.

The specific strain of *Micrococcus varians* preferably used in the compositions of the present invention is available from the American Type Culture Collection No. 15,306 and is the neotype strain as described in Bergey's Manual of Determinative Bacteriology (8th Ed., 1974) pages 481 and 482. The culture is available from the American Type Culture Collection without restrictions. It is deposited with the USDA Regional Laboratory in Peoria, Ill. as NRRL-B-11,060. It is used to develop a superior flavor in fermented meats.

*Micrococcus varians* is a relatively very poor acid producer. It can produce a red color change in the meat with edible nitrite and/or an edible nitrate. Acid is necessary in the formation of nitric oxide from the nitrite which reacts with components of the meat to form the red color, and thus *Micrococcus varians* is used with selected meat fermenting lactic acid producing bacteria for color change. The use of added acids (such as GDL) is avoided.

A problem with the nitrate reducing bacteria used by the prior art is that the nitrate reductase enzymes are pH sensitive. Acid producing chemicals, such as GDL, cannot be used for this reason. Depending upon the particular species of bacterium, the nitrate reducing activity is terminated when a particular acid level is achieved. With NRRL-B-8048, described in U.S. Pat. No. 4,013,797, this pH is about 5.6; however, NRRL-B-8048 reduces nitrate rapidly enough so that reduction is completed within the time period that the pH is higher that 5.6 in the sausage. Most other Micrococcus are much slower than NRRL-B-8048 in reducing nitrate and if reduction was terminated at about pH 5.6, nitrate would be incompletely reduced. *Micrococcus varians* ATCC 15,306 is not inhibited in its nitrate reducing function until a pH of about 5.2 is achieved and thus ideally suited for the compositions of the present invention.

The "gray ring" which is a color defect seen in fully dried sausage, can also be prevented with the compositions of the present invention using *Micrococcus varians*. The defect is evidenced by a gray ring around the casing. The defect is believed to be caused by accumulations of hydrogen peroxide and the bacterial compositions including *Micrococcus varians* may generate catalase enzyme which dissipates the hydrogen peroxide.

*Micrococcus varians* by generating nitrites from the edible nitrates can also help prevent the growth of botulism toxin bacteria. Smaller amounts of edible nitrites can be used for the initial antimicrobial action in making meat products according to the present invention. *Micrococcus varians* acts to produce a red color in the presence of small amounts of nitrate even in absence of the nitrite and amounts less than about 200 ppm nitrate produce this result. Usually about 50 to 90 ppm nitrite are regarded as necessary as a minimum to initially prevent the growth of botulism bacteria. The *Micrococcus varians* is used in a ratio of Micrococcus to malty flavor producing culture of 1.0 to 0.01 and 1.0 to 1.0 by cell count.

In the method of this invention, using the cultures which produce 3-methyl-butanal, lactic acid producing bacteria can be used such as the *Pediococcus acidilactici*, *Pediococcus pentosaceus* or *Lactococcus lactis* in combination with *Micrococcus varians*. It has been found that the flavor of dry and semi-dry sausages is particularly improved by using *Pediococcus acidilactici* as the lactic acid producing bacterium. *Pediococcus cerevisiae* NRRL-B-5627, which is freely available from the USDA, is particularly preferred since it inhibits the development of undesirable putrefying or contaminating bacteria such as *Staphylococcus aureus* as well as rapidly producing lactic acid. Other cultures which produce lactic acid can be used, such as Streptococcus sp.

In the process of making sausage, the conventional steps are carried out. Thus, the proper selection of a single meat or different meats is chopped and mixed either separately or together. The next step is that of adding and mixing the curing agents including edible nitrates or edible nitrites or mixtures thereof, salt, dextrose (or other suitable carbohydrates) and spices. This selection and the relative amounts conform to standard practices. The bacterial concentrate is added during the mixing of the other components of the sausage, usually the mixing is at a low temperature.

In one sausage making process of this invention, a culture composition of the malty flavor producing culture, *Micrococcus varians* and the lactic acid producing meat fermenting bacteria in an amount between 0.0001% and 10% (0.000001 to 0.1 parts per part of meat) based on the weight of the meat and usually containing between about $10^7$ to $10^{12}$ cells per ml, is added to the meat mixture as soon as it is ground. Preferably the composition is used at a level of $10^5$ to $10^9$ bacteria per gram of meat. Also preferably the bacterial concentrate described previously containing at least about $10^9$ cells per ml is used. Sausage prepared in this manner is stuffed into casings and preferably fermented at a temperature of 41° F. to 125° F. (5° C. to 52° C.) for periods of about six (6) hours or more depending upon the concentration of culture used. In the preferred process of the present invention, the ratio of *Micrococcus varians* to lactic acid bacteria by bacterial count is between 1 to 1 and 1 to 8. The culture which produces the 3-methyl-butanal is used in the cell count ratios discussed above in relation to the lactic acid producing bacterium.

The following Example 1 shows that a unique tasting salami is produced in pilot plant trials using the *Lactococcus lactis* spp *lactis* NRRL-B-21904 and that the use of this culture with a commercial culture did not interfere with the commercial production of the salamis. Example 2 shows a trial on a commercial scale. Example 3 shows an industrial scale trial with a Lactobacillus which produces 3-methyl-butanal.

EXAMPLE 1

Materials and Methods

Cultures: For the normal starter, a commercial frozen concentrate of *Pediococcus pentosaceus* (SAGA 75 Quest International, Rochester, Minn. as described in U.S. Pat. No. 4,303,679 with manganese (13 parts per million)) was used at the recommended usage rate of 40.8 g/200 kg of meat. The malty *Lactococcus lactis* spp *lactis* NRRL-B-21904 (CJW-8) was a raw milk isolate. The concentrated cultures contained about $10^{11}$ CFU/gram. The species identification of the strain was made using biochemical tests and nucleic acid probes.

Sausage Manufacture: The percentages are by weight. Sausages were made in pilot-plant scale trials. The formulation used was as follows: lean beef—40%; lean pork—30%; back fat 30%. Nitrited salt 3% (0.6% sodium nitrite); dextrose 0.5%; salami spices 0.1% were added to the meat block. The batch size was 4.0 kg.

Meat held at −8° C. was ground separately. Each batch was chopped at low speed and the culture(s) added and mixed throughly. This was followed by other ingredients, which were also mixed in uniformly. Throughout the mixing process, the meat mixture was kept as cold as possible to prevent smearing of fat. The meat mixture was then stuffed into permeably casings and placed in a fermentation chamber held at 20° C. at a relative humidity (R.H.) of 95% for three (3) days. At the end of three (3) days, the conditions were changed to 14° C. and relative humidity of 75% and the sausages were held for a further period of 15 to 20 days. The study included two treatments: (1) Control: SAGA 75 (S-75), *Pediococcus pentosaceus;* and (2) SAGA 75 (S-75) *Pediococcus pentosaceus* and *Lactococcus lactis* spp *lactis* CJW-8 (*L. lactis*) in a cell ratio of one to one. The trials were repeated two times, results were averaged.

Fermentation parameters: The sausages were analyzed for pH, lactic acid, total sugars, moisture and fat content.

Microbiological analyses: Total lactic acid producing bacteria were determined on MRS agar at 30° C. at time 0, 1, 4, 10 and 20 days fermentation. For safety reasons, Enterobacteriaceae, *S. aureus,* Enterococci, gram negatives, yeast/molds, spore formers and Salmonella were determined (values not given) and were found to be acceptable.

Sensory analyses: The results of panel testing are shown in Table 1.

TABLE 1

|  | AROMA | | | FLAVOR | | |
|---|---|---|---|---|---|---|
|  | Acid | Salami | Off-notes | Acid | Salami | Off-notes |
| L. lactis spp. lactis | 7.7 | 7.7 | 4.3 | 7.2 | 7.9 | 4.2 |
| SAGA 75 | 6.0 | 5.7 | 6.7 | 5.7 | 5.8 | 6.3 |

Sausages with *Lactococcus lactis* spp *lactis* (CJW8) had considerably higher scores for salami aroma and flavor as compared to the reference. The reference was found less acid and with off-notes by the panelists.

Sensory analysis was conducted by using a 15-cm line scale. The taste panel members were qualified flavorists. Samples cut into slices from the two treatments were presented simultaneously to 10 panelists. The samples were scored on a 15-cm line by placing a slash perpendicular to the line at the point that best describes the attributes for aroma and flavor: acid (0=not acid, 15=very acid), salami (0=none, 15=intense), off-notes (0=none, 15=intense). The score for each attribute was measured (cm) by using a ruler from the left hand side of the 15-cm line scale, and the scores obtained were averaged to give the final score for each attribute.

Mass spectometry: This is shown in Table 2.

The salamis were analyzed for components resulting from the fermentations. 3-methyl-butanal is a significant component.

TABLE 2

| RRT | Time | Name | S75 and Lactis | Control S75 |
|---|---|---|---|---|
| 478.2 | 3.766 |  |  | 14.8 |
| 482.5 | 3.800 | ethanol | 1.0 |  |
| 496.8 | 4.653 |  |  | 2.7 |
| 561.5 | 5.886 | dichloro ethylene | 6.0 |  |
| 586.1 | 6.360 |  | 4.4 | 2.7 |
| 613.2 | 7.093 |  | 2.2 | 1.6 |
| 623.4 | 7.473 | isobutanol | 10.0 | 4.5 |
| 649.7 | 8.446 | isovaleraldehyde (3-methyl-butanal) | 1.8 | 0.2 |
| 702.1 | 10.426 | methyl allyl sulphide | 4.6 | 4.5 |
| 708.0 | 10.773 | acetoine | 15.9 | 12.5 |
| 728.9 | 11.966 | 3-methyl-butanal | 7.9 | 5.3 |
| 732.9 | 12.193 | 2-methyl butanal | 1.1 |  |
| 734.5 | 12.293 | isobutyric acid | 2.0 | 2.0 |
| 751.8 | 13.280 |  | 1.1 | 1.0 |
| 760.9 | 13.800 | pentanol | 3.7 | 3.0 |
| 765.4 | 14.060 | butyric acid | 9.0 | 9.1 |
| 769.7 | 14.306 |  | 1.1 | 1.0 |
| 784.3 | 15.140 |  | 1.1 | 0.8 |
| 790.6 | 15.506 |  | 1.1 | 0.8 |
| 800.4 | 16.080 | aldehyde C6 | 21.0 | 15.8 |
| 812.2 | 16.960 | ethyl lactate | 1.1 | 1.2 |
| 827.7 | 18.140 | 3-methyl butyric acid | 31.3 | 21.2 |
| 832.7 | 18.500 | furfural | 3.1 | 3.3 |
| 835.6 | 18.720 | 2-methyl butyric acid | 4.5 | 2.5 |
| 839.5 | 19.013 | diaceton alcohol | 7.5 | 1.3 |
| 851.1 | 19.880 | 2-hexenal | 3.1 | 2.4 |
| 864.7 | 20.900 | alcohol C6 | 3.5 | 3.9 |
| 901.8 | 23.706 | aldehyde C7 | 6.2 | 4.8 |
| 907.1 | 24.140 | methional | 1.5 | 1.0 |
| 913.5 | 24.673 | gamma-butyrolacton | 1.0 | 0.5 |
| 925.5 | 25.666 |  | 1.2 | 1.3 |
| 933.0 | 26.286 |  | 1.8 | 2.2 |
| 941.2 | 26.966 | alpha-pinene | 1.8 | 2.2 |
| 957.3 | 28.306 | camfene | 5.4 | 5.6 |
| 967.0 | 29.126 | hexanoic acid | 25.9 | 29.1 |
| 978.1 | 30.040 | octen-1-ol-3(primaverol) | 2.9 | 3.6 |
| 980.4 | 30.226 | sabinene | 4.9 | 6.1 |
| 982.3 | 30.386 | octandion-2,3 | 2.5 | 2.5 |
| 986.3 | 30.720 | beta-pinene | 3.8 | 4.1 |
| 990.3 | 31.046 |  | 1.2 |  |
| 993.8 | 31.340 | 2-pentyl furan | 4.9 | 5.9 |
| 1003.9 | 32.180 | aldehyde C8 | 5.9 | 5.1 |
| 1012.7 | 32.920 | 2,4-heptadienal | 3.2 | 3.3 |
| 1018.2 | 33.380 | paramenthadiene | 3.4 | 3.3 |
| 1028.2 | 34.213 |  | 1.2 | 0.7 |
| 1031.4 | 34.480 | paracymene | 1.1 | 1.2 |
| 1036.1 | 34.880 | limonene + benzyl alcohol | 5.4 | 11.3 |
| 1038.5 | 35.080 | 2-methyl-3-ethyl-1,3-hexadiene | 3.0 | 2.7 |
| 1040.3 | 35.226 | eucalyptol | 1.4 | 1.2 |
| 1050.3 | 36.066 | phenyl acetaldehyde | 5.9 | 5.2 |
| 1060.3 | 36.906 | 2-octenal | 3.7 | 4.2 |
| 1062.2 | 37.066 | gamma-terpinene | 2.2 | 2.0 |
| 1065.6 | 37.346 |  | 1.2 | 2.2 |
| 1069.2 | 37.653 | paramenthadiene | 2.3 | 2.2 |
| 1072.0 | 37.886 | paracresol | 1.5 | 1.3 |
| 1096.4 | 39.926 |  | 2.4 | 1.8 |
| 1097.9 | 40.053 |  | 1.0 | 1.5 |
| 1101.9 | 40.386 | linalool | 7.6 | 7.9 |
| 1105.9 | 40.720 | aldehyde C9 | 27.2 | 15.1 |
| 1120.3 | 41.886 | beta-phenylethyl alcohol | 4.0 | 3.1 |
| 1150.8 | 44.366 |  | 1.1 | 1.1 |
| 1163.2 | 45.380 | octanoic acid + 2-nonenal | 56.8 | 60.8 |
| 1170.8 | 45.993 | alcohol C9 | 2.3 | 2.1 |
| 1189.5 | 47.520 | terpinene-4-ol | 2.6 | 2.9 |
| 1190.8 | 47.626 | butyl diglycol | 2.9 |  |
| 1199.9 | 48.366 | styrallyl acetate + alpha-terpineol | 5.1 | 4.9 |
| 1207.9 | 48.986 | aldehyde C10 | 2.0 | 1.1 |
| 1230.0 | 50.693 | nerol | 1.2 | 1.8 |
| 1247.9 | 52.080 | neral | 1.0 | 1.1 |
| 1252.1 | 52.406 |  | 1.1 | 1.2 |
| 1258.9 | 52.933 | nonanoic acid + linalyl acetate + geraniol | 7.7 | 6.1 |
| 1266.0 | 53.486 | 2-decenal | 7.6 | 9.6 |
| 1295.7 | 55.780 |  | 1.0 | 1.1 |

TABLE 2-continued

| RRT | Time | Name | S75 and Lactis | Control S75 |
|---|---|---|---|---|
| 1299.3 | 56.060 | 2,4-decadienal (1) | 8.2 | 10.1 |
| 1302.4 | 56.286 | saffrol + indol | 3.1 | 3.6 |
| 1323.0 | 57.800 | 2,4-decadienal (2) | 17.8 | 23.8 |
| 1331.2 | 58.400 | styrallyl (iso)butyrate | 2.0 | 1.7 |
| 1352.9 | 59.986 | 2-undecenal (1) | 9.7 | 11.0 |
| 1361.7 | 60.653 | decanoic acid ? | 137.5 | 149.1 |
| 1369.2 | 61.180 | terpinyl acetate + 2-undecenal (2) | 10.0 | 9.8 |
| 1377.7 | 61.806 | sesq.terp. | 2.4 | 3.1 |
| 1386.2 | 62.426 | sesq.terp. | 3.1 | 1.2 |
| 1392.8 | 62.913 | | 1.4 | 1.0 |
| 1395.1 | 63.080 | ethyl decanoate + skatol | 1.0 | 1.1 |
| 1409.4 | 64.093 | methyl eugenol | 1.3 | 1.4 |
| 1432.8 | 65.713 | sesq.terp. | 1.2 | 1.4 |
| 1447.9 | 66.760 | beta-caryofyllene | 11.3 | 13.6 |
| 1456.5 | 67.353 | | 1.3 | 1.6 |
| 1463.2 | 67.820 | | 1.2 | 1.6 |
| 1476.1 | 68.720 | alcohol C12 | 1.1 | 0.4 |
| 1482.5 | 69.160 | | 1.2 | 1.4 |
| 1485.7 | 69.380 | | 1.6 | 1.5 |
| 1499.3 | 70.326 | tridecanon-2 | 9.6 | 9.1 |
| 1511.2 | 71.106 | delta-lacton C10 | 2.5 | 2.5 |
| 1527.3 | 72.160 | bht | 1.0 | 2.2 |
| 1538.2 | 72.873 | myristicine | 10.0 | 11.6 |
| 1557.8 | 74.160 | lauric acid ? | 35.6 | 28.9 |
| 1580.2 | 75.626 | an aldehyde C14 | 2.5 | 2.1 |
| 1587.7 | 76.113 | | 1.3 | 0.4 |
| 1593.5 | 76.493 | | 1.4 | 1.1 |
| 1609.0 | 77.480 | | 1.4 | 0.4 |
| 1617.5 | 78.006 | aldehyde C14 | 4.5 | 4.5 |
| 1682.2 | 82.046 | | 1.5 | 1.7 |
| 1690.8 | 82.580 | an aldehyde C15 | 1.8 | 2.1 |
| 1694.5 | 82.806 | gamma-lacton C12 | 1.6 | 1.8 |
| 1702.5 | 83.300 | pentadecanon-2 | 25.2 | 25.5 |
| 1707.0 | 83.560 | 2,6,10,14-tetramethyl pentadecane | 14.0 | 3.6 |
| 1719.7 | 84.306 | aldehyde C15 | 4.3 | 4.6 |
| 1727.5 | 84.766 | delta-lacton C12 | 3.8 | 3.9 |
| 1748.6 | 86.020 | | 1.0 | 1.8 |
| 1758.4 | 86.593 | myristic acid | 16.2 | 18.0 |
| 1784.8 | 88.153 | an aldehyde C16 | 3.9 | 2.4 |
| 1790.4 | 88.480 | octadecene | 11.8 | 15.3 |
| 1800.0 | 89.046 | alkane C18 | 4.2 | |
| 1807.5 | 89.466 | | 1.9 | 0.2 |
| 1811.9 | 89.713 | | 2.1 | 1.7 |
| 1822.1 | 90.306 | aldehyde C16 | 113.7 | 123.4 |
| 1836.0 | 91.073 | | 1.0 | |
| 1842.8 | 91.460 | | 2.1 | 2.6 |
| 1849.5 | 91.833 | nonadecene | 5.1 | 6.4 |
| 1883.9 | 93.766 | diisobutyl phtalate | 1.4 | |
| 1887.2 | 93.953 | heptadecanon-2 | 2.7 | 3.0 |
| 1896.4 | 94.466 | aldehyde C17 | 4.1 | 3.9 |
| 1906.7 | 95.033 | gamma-lacton C14 | 4.8 | 4.9 |
| 1924.5 | 95.993 | aldehyde C17 | 4.0 | 4.3 |
| 1943.7 | 97.026 | | 3.4 | 3.0 |
| 1979.1 | 98.933 | dibutyl phtalate | 4.8 | 1.6 |
| 2006.4 | 100.386 | an aldehyde C18 | 13.5 | 19.1 |
| 2010.2 | 100.580 | an aldehyde C18 | 3.7 | 1.0 |
| 2027.0 | 101.446 | aldehyde C18 | 22.9 | 23.9 |
| 2159.5 | 108.126 | an acid | 3.2 | 2.7 |
| 2562.7 | 132.293 | dioctyl phtalate | 2.3 | 8.6 |

RRT: Retention time compared to authentic compounds

Figure 1:
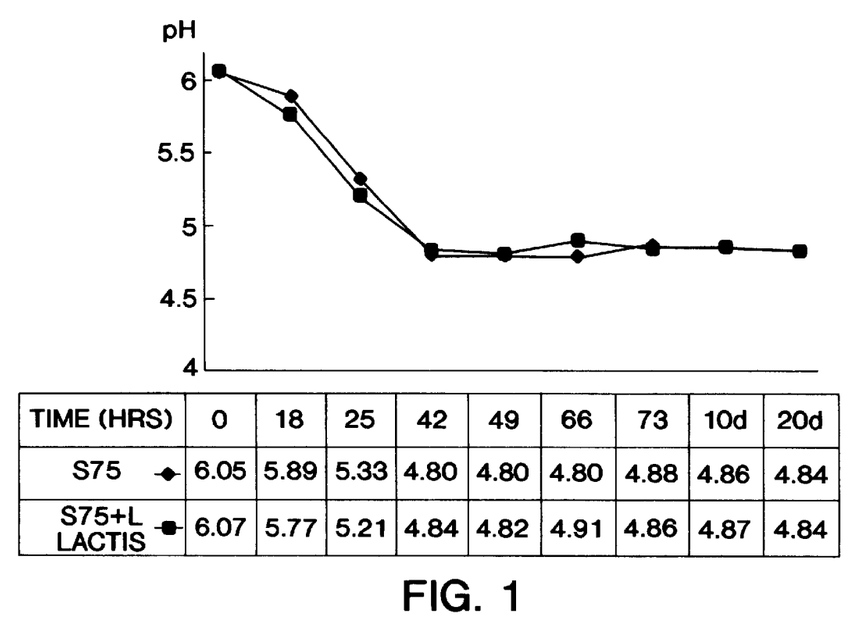
FIG. 1 is a graph showing pH as a function of time in salamis with *Pediococcus pentosaceus* (S75) and with *Lactococcus lactis* spp *lactis* (S75+L. *lactis*).
Figure 2:
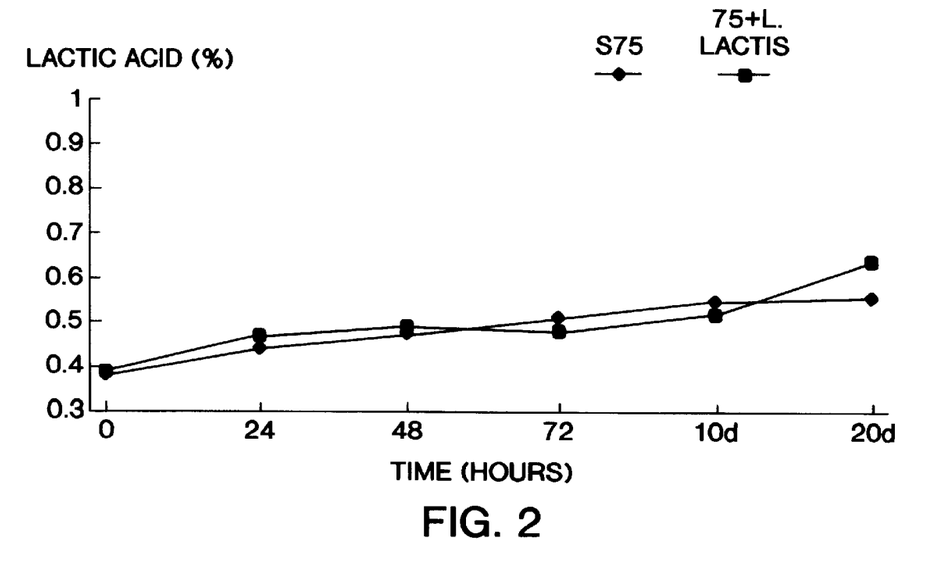
FIG. 2 is a graph showing the lactic acid production as a function of time for the fermentations of FIG. 1.
Figure 3:
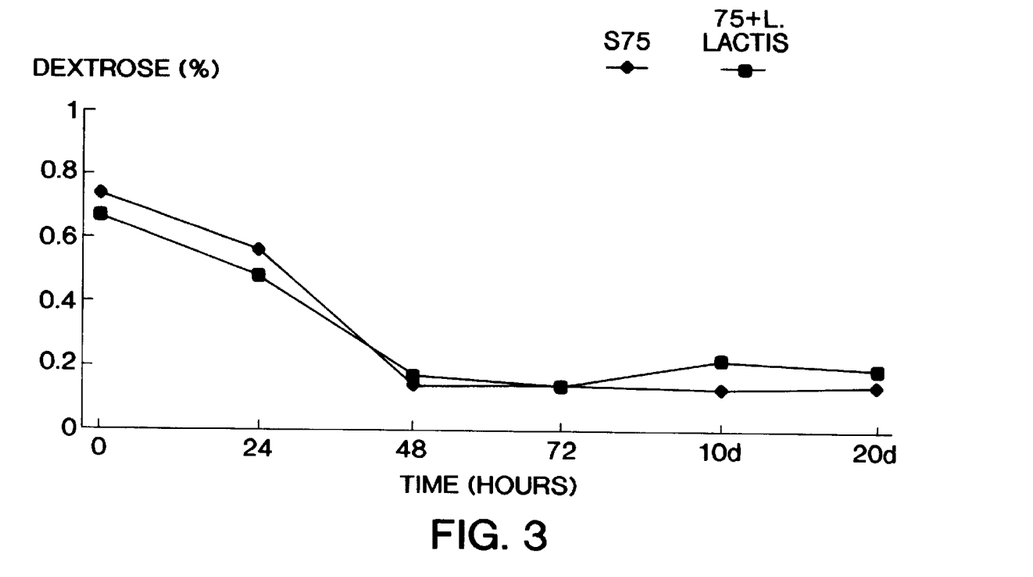
FIG. 3 is a graph showing residual sugar content (primarily dextrose) in the salamis as a function of time for the fermentations of FIG. 1.
Figure 4:
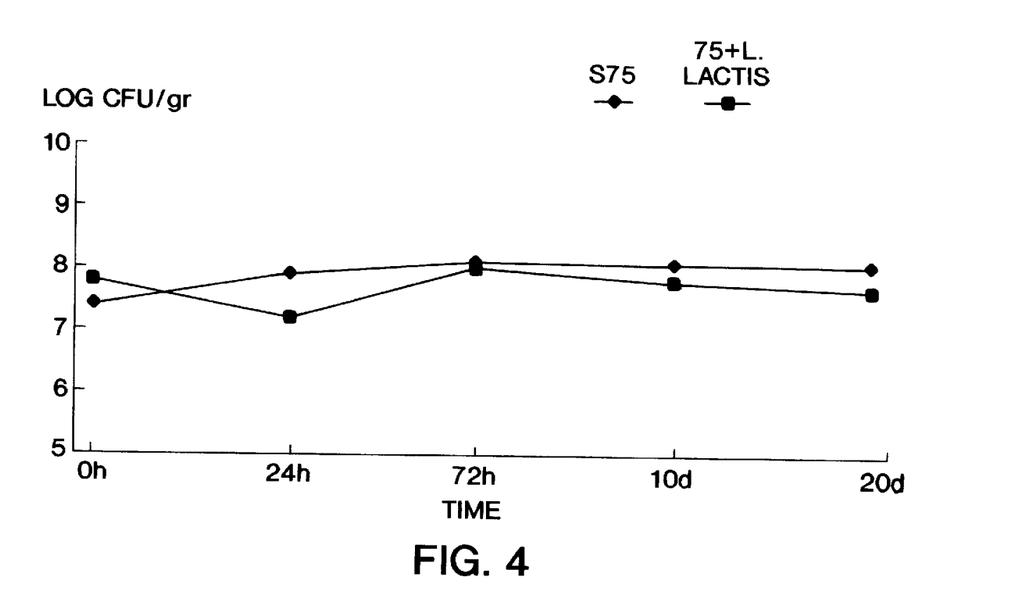
FIG. 4 is a graph showing total lactic acid producing bacteria (by cell count of cell forming units (CFU)) present in the salamis at 30° C. as a function of time for the fermentations of FIG. 1.
Figure 5:
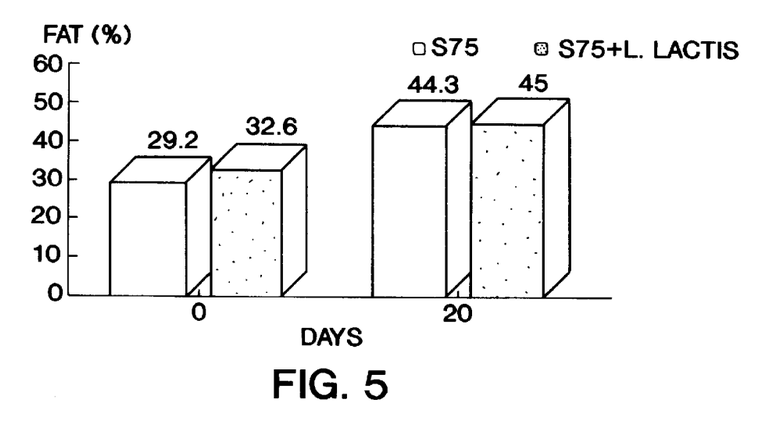
FIG. 5 is a graph showing fat content of the salamis of FIG. 1 as a function of time.
Figure 6:
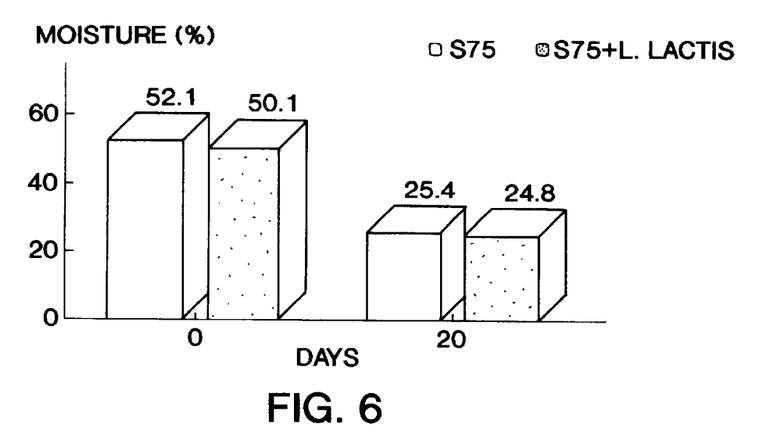
FIG. 6 is a graph showing moisture content of the salamis of FIG. 1 as a function of time.
Figure 7:
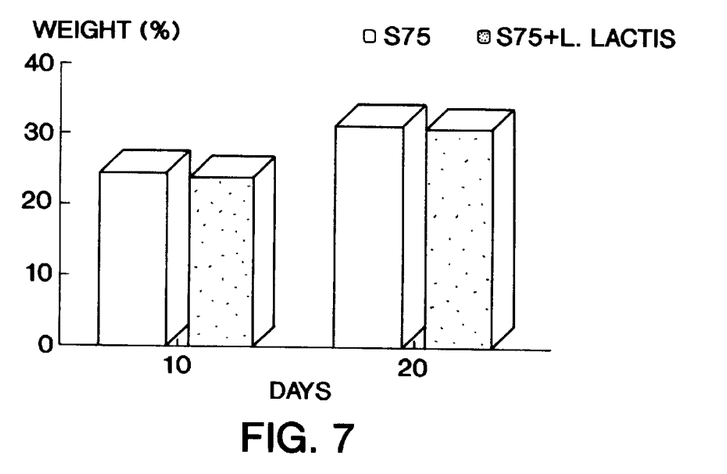
FIG. 7 is a graph showing weight loss (primarily moisture) of the salamis of FIG. 1 as a function of time.

Fermentation parameters. The pH curve showed no difference between treatments. Final pH was reached at 42 hours (FIG. 1). Lactic acid production increased steadily and equally during fermentation and drying for the two types of sausages (FIG. 2). Residual sugars decreased also constantly and equally for the two treatments (FIG. 3). FIG. 4 shows the bacterial content was normal, Fat content (FIG. 5), moisture (FIG. 6), and weight (FIG. 7) were normal. Thus the *Lactococcus lactis* spp lactis does not interfere with the normal sausage fermenting.

EXAMPLE 2

Salamis with and without *Lactococcus lactis* spp *lactis* NRRL-B-21904 (CJW8) were produced on industrial scale. The starter cultures in the standard formula were as follows:

SAGA 482 (*S. carnosus*) (peroxide reduction) and (*P. pentosaceus*) (lactic acid producing)

SAGA 777 (*L. sake*) (lactic acid producing)

SAGA 445 (*M. varians*) (red color) (Quest International, Rochester, Minn.) in a ratio by cell count which was about equal. The concentrates contained about $10^{11}$ CFU.

One batch was prepared with the standard formula and one with the same formula plus the addition of the Lactococcus strain. The other ingredients used were: sugar blend (saccharose, dextrose, Kristallpur); spices; sodium ascorbate; and BIOPHEROL 3401 (rosemary extract). The salamis were fermented until a final pH of 4.7–4.8 and dried at 15–16° C. until desired firmness. The final pH was 4.9.

The two sausages showed the same fermentation pattern as in Example 1. The final product was then evaluated by a 9-member trained sensory panel. Seven out of the total panelists chose the salami with the Lactococcus strain and the sausage was described as less acid with more fermented and nutty notes. The spices were perceived stronger in the salami with the Lactococcus strain and the overall taste was more round and full.

EXAMPLE 3

*Lactobacillus maltaromicus* ATCC 27865 was isolated from a sample of raw milk, from a farm, that had a malty flavor. The organism produced besides lactic acid, different aldehydes and alcohols such as 2-methylpropionaldehyde, 2-methylpropanal, 3-methylbutyraldehyde and 3-methyl-butanal in milk and trypticase soy broth. Previously, it was reported that 3-methyl-butanal was the compound responsible for malty flavor found in milk cultures of certain *Lactococcus lactis* spp. *lactis* strains (formerly called *Streptococcus lactis* var. *maltigenes*). Because 3-methyl-butanal is associated with the typical flavor in certain fermented meats like salami, pepperoni, etc., the effect of adding *Lactobacillus maltaromicus* ATCC 27865, as an adjunct culture in sausage manufacture was tried on a pilot plant scale. The objective for this trial was to evaluate the effect of using this strain as an adjunct culture in sausage manufacture, on the final flavor profile of the finished sausage.

Starter Culture(s)

Control Sausage: SAGA 75 (*Pediococcus pentosaceus* of Example 1) Rate: 40.8 g/200 Kg meat diluted 1/10 to 8.0 ml (The undiluted culture had 110 billion colony forming units/ml.)

Experimental Sausage: SAGA 75 as in the Control plus *Lactobacillus maltaromicus* 14.0 ml of undiluted culture (The culture had 11 billion colony forming units/ml.)

The details of the experiment were as follows: Sausage Formulation: Lean Beef 400 g; Lean Pork 300 g; Back fat 300 g; Nitrited salt 30 g (0.6% sodium nitrite); Dextrose 5 g; and Salami spices 1 g. Batch size was 4 Kg.

The meat was ground separately for the variables. Each batch was chopped at low speed and the culture or cultures were added. Once mixed, the rest of the ingredients were added. The meat mixture was then stuffed in permeable casings, and the sausages were placed in the fermentation cabinet. For the first three days, the temperature was maintained at 20° C., and the relative humidity was controlled at 95%. Then the temperature and relative humidity were adjusted to 14° C., and 75% respectively. The sausages were held under these conditions for 15 to 20 days.

Results: The control sausage at the end of stuffing had a pH of 6.11. After 18, 25, 42, 49, 66 and 73 h, the pH values were 5.22, 4.88, 4.90, 4.93, 4.95 and 4.90, respectively. After 10 days and 20 days the values were 4.96 and 5.01 respectively. The experimental sausage started at pH 5.93 and for similar sampling intervals, the pH values were 5.19, 4.78, 4.59, 4.59, 4.57, 4.62, 4.64 and 4.62, respectively. There were no appreciable differences in the weight losses of the two sausages. There were no color differences between the two sausages.

The concentrations of 3-methyl-butanal and 2-methyl butanal (which are both important flavor components in sausages) were, however, different. These components were undetectable in the control sausage, but the experimental sausage contained 3 mg/Kg of 3-methyl-butanal and 1 mg/Kg of 2-methyl butanal.

The sensory evaluation by a 7-member panel found the experimental sausage containing the Lactobacillus strain to be more "acidic" in flavor. The off-notes in the control sausage had a score of 6.6, while the experimental received a score of 5.4. The score was set up on a scale of 0 to 15, zero being no off-notes and 15 representing very intense off-notes, as in Example 1. The overall results showed that *Lactobacillus maltaromicus* could be used as an adjunct starter in sausages to increase the 3-methyl-butanal content.

It is intended that the foregoing description be only illustrative of the present invention and that the present invention be limited only by the hereinafter appended claims.

We claim:

1. In a method of meat fermentation with a lactic acid producing bacterium, an assimilable carbohydrate and a nitrate or nitrite salt in the meat to produce a fermented meat, the improvement which comprises:
   (a) mixing in the meat a culture comprising a first bacterium selected from the group consisting of a Lactococcus and a Lactobacillus which each produce 3-methyl-butanal from leucine with a lactic acid producing second bacterium which produces the leucine, wherein the culture contains a manganese salt in an amount which stimulates fermentation by the second bacteria, in cell numbers of the culture which provide flavor and aroma from the first and the second bacterium in the fermented meat, wherein the first bacterium is identified as producing the 3-methyl-butanal as a malty flavor in milk and as a flavor in the meat and is tolerant of the nitrate or nitrite salt in the meat; and
   (b) fermenting the meat to produce the fermented meat.

2. In a method of meat fermentation comprising the steps of providing a lactic acid producing bacterium with an assimilable sugar and a nitrate or nitrite salt in the meat so that the lactic acid is produced from the sugar over a period of time to produce the fermented meat, the improvement which comprises:
   (a) mixing in the meat a culture comprising a first bacterium selected from the group consisting of a Lactococcus and a Lactobacillus which each produce 3-methyl-butanal from leucine with the lactic acid producing second bacterium which produces the leucine, wherein the culture contains a manganese salt in an amount which stimulates fermentation by the second bacterium, in cell numbers of the culture which provides flavor and aroma from the first and the second bacterium in the fermented meat, wherein the first bacterium is identified as being isolated from and also producing the 3-methyl-butanal as a malty flavor in milk and is tolerant of the nitrate or nitrite salt in the meat; and
   (b) fermenting the meat to produce the fermented meat.

3. The method of claim 2 wherein the fermented meat is a sausage.

4. The method of claim 2 wherein the fermented meat is a dried sausage.

5. The method of claim 4 wherein the sausage is a salami.

6. The method of any one of claims 2, 3, 4 or 5 wherein the first bacterium is *Lactococcus lactis* subspecies *lactis* deposited as NRRL-B-21904 (CJW-8).

7. The method of claim 2 wherein the pH of the fermented meat is less than or equal to pH 5.

8. The method of claim 2 wherein the lactic acid producing second bacterium is a Pediococcus.

9. The method of claim 8 wherein the Pediococcus is *Pediococcus pentosaceus*.

10. The method of claim 8 wherein the Pediococcus is *Pediococcus cerevisiae*.

11. The method of claim 2 wherein a Micrococcus as an additional culture for red color development is provided in the meat.

12. The method of claim 11 wherein the Micrococcus is *Micrococcus varians*.

13. The method of claim 12 wherein the culture includes a third bacterium which provides red color development and reduces hydrogen peroxide in the fermented meat.

14. A bacterial culture for a meat fermentation in the presence of a nitrate or nitrite salt which comprises:
   (a) a lactic acid producing first bacterium which produces lactic acid from an assimilable sugar in the meat and produces leucine;
   (b) a second bacterium selected from the group consisting of a Lactococcus and a Lactobacillus which produces 3-methyl-butanal from the leucine in the meat in cell numbers which provides flavor and aroma from the first and the second bacterium when mixed in the fermented meat, wherein the second bacterium is identified as producing the 3-methyl-butanal as a malty flavor in milk and as a flavor in the meat and is tolerant of the nitrate or nitrite salt in the meat; and
   (c) a manganese salt in an amount which stimulates fermentation by the second bacterium.

15. The culture of claim 14 wherein the lactic acid producing first bacterium is Pediococcus.

16. The culture of claim 15 wherein the Pediococcus is *Pediococcus pentosaceus*.

17. The culture of claim 15 wherein the Pediococcus is *Pediococcus cerevisiae*.

18. The culture of any one of claims 14 or 15 wherein the second bacterium is *Lactococcus lactis* subspecies *lactis* deposited as NRRL-B-21904.

19. The culture of claim 14 wherein the culture contains *Lactococcus lactis* subspecies *lactis* as the second bacterium which produces the 3-methyl-butanal and wherein the culture contains the cell numbers of at least about $10^6$ CFU per ml and in a ratio of between about 1 to 10 and 10 to 1 of the lactic acid producing bacterium to the *Lactococcus lactis* subspecies *lactis*.

20. The culture of claim 19 wherein the culture contains between about $10^6$ and $10^{12}$ CFU per ml.

21. The culture of claim 14 where an additional third bacterium for red color development is provided in the meat.

22. The culture of claim 21 wherein the third bacterium is *Micrococcus varians*.

23. The culture of claim 14 wherein an additional third bacterium is provided the culture which produces red color development and dissipates hydrogen peroxide in the meat fermentation.

24. In a method of meat fermentation with a lactic acid producing bacterium, an assimilable carbohydrate and a nitrate or nitrite salt in the meat to produce a fermented meat, the improvement which comprises:

(a) mixing in the meat a culture comprising a first bacterium selected from the group consisting of *Lactococcus lactis* spp *lactis* NRRL-B-21904 and *Lactobacillus maltaromicus* ATCC 27865 which each produce 3-methyl-butanal from leucine with a lactic acid producing second bacterium which produces the leucine in cell numbers of the culture which provide flavor and aroma from the first and the second bacterium in the fermented meat; and (b) fermenting the meat to produce the fermented meat.

25. In a method of meat fermentation comprising the steps of providing a lactic acid producing bacterium with an assimilable sugar and a nitrate or nitrite salt in the meat so that the lactic acid is produced from the sugar over a period of time to produce the fermented meat, the improvement which comprises:

(a) mixing in the meat a culture comprising a first bacterium selected from the group consisting of *Lactococcus lactis* spp *lactis* NRRL-B-21904 and *Lactobacillus maltaromicus* ATCC 27865 which each produce 3-methyl-butanal from leucine with the lactic acid producing second bacterium which produces the leucine in cell numbers of the culture which provides flavor and aroma from the first and the second bacterium in the fermented meat; and (b) fermenting the meat to produce the fermented meat.

26. The method of claim 25 wherein the fermented meat is a sausage.

27. The method of claim 25 wherein the fermented meat is a dried sausage.

28. The method of claim 27 wherein the sausage is a salami.

29. The method of claim 25 wherein the pH of the fermented meat is less than or equal to pH 5.

30. The method of claim 25 wherein the lactic acid producing second bacterium is a Pediococcus.

31. The method of claim 30 wherein the Pediococcus is *Pediococcus pentosaceus*.

32. The method of claim 30 wherein the Pediococcus is *Pediococcus cerevisiae*.

33. The method of claim 25 wherein a Micrococcus as an additional culture for red color development is provided in the meat.

34. The method of claim 33 wherein the Micrococcus is *Micrococcus varians*.

35. The method of claim 34 wherein the culture includes a third bacterium which provides red color development and reduces hydrogen peroxide in the fermented meat.

36. A bacterial culture for a meat fermentation in the presence of a nitrate or nitrite salt which comprises:

(a) a lactic acid producing first bacterium which produces lactic acid from an assimilable sugar in the meat and produces leucine; and (b) a second bacterium selected from the group consisting of *Lactococcus lactis* spp *lactis* NRRL-B-21904 and *Lactobacillus maltaromicus* ATCC 27865 which produces 3-methyl-butanal from the leucine in the meat in cell numbers which provides flavor and aroma from the first and the second bacterium when mixed in the fermented meat.

37. The culture of claim 36 wherein the lactic acid producing first bacterium is a Pediococcus.

38. The culture of claim 37 wherein the Pediococcus is *Pediococcus pentosaceus*.

39. The culture of claim 37 wherein the Pediococcus is *Pediococcus cerevisiae*.

40. The culture of claim 36 wherein the culture contains the *Lactococcus lactis* subspecies *lactis* NRRL-B-21904 as the second bacterium which produces the 3-methyl-butanal and wherein the culture contains the cell numbers of at least about $10^6$ CFU per ml and in a ratio of between about 1 to 10 and 10 to 1 of the lactic acid producing bacterium to the *Lactococcus lactis* subspecies *lactis*.

41. The culture of claim 40 wherein the culture contains between about $10^6$ and $10^{12}$ CFU per ml.

42. The culture of claim 36 where an additional third bacterium for red color development is provided in the meat.

43. The culture of claim 42 wherein the third bacterium is *Micrococcus varians*.

44. The culture of claim 36 wherein an additional third bacterium is provided the culture which produces red color development and dissipates hydrogen peroxide in the meat fermentation.

45. The method of claim 24 wherein the culture of the second bacterium contains a manganese salt.

46. The method of claim 25 wherein the culture of second bacterium contains a stimulators amount of a manganese salt.

47. The bacterial culture of claim 36 which culture contains an amount of a manganese salt which stimulates fermentation by the second bacterium in the meat.

* * * * *